United States Patent
Sartorius et al.

(10) Patent No.: US 8,953,937 B2
(45) Date of Patent: Feb. 10, 2015

(54) ARRANGEMENT FOR GENERATING A SIGNAL HAVING AN ADJUSTABLE TIME POSITION OR PHASE POSITION

(75) Inventors: Bernd Sartorius, Berlin (DE); Helmut Roehle, Berlin (DE); Dennis Stanze, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 154 days.

(21) Appl. No.: 13/514,168
(22) PCT Filed: Feb. 11, 2011
(86) PCT No.: PCT/EP2011/000858
§ 371 (c)(1), (2), (4) Date: Jan. 30, 2013
(87) PCT Pub. No.: WO2011/134562
PCT Pub. Date: Nov. 3, 2011

(65) Prior Publication Data
US 2013/0121687 A1 May 16, 2013

(30) Foreign Application Priority Data
Apr. 30, 2010 (DE) .......................... 10 2010 019 134

(51) Int. Cl.
*H04B 10/08* (2006.01)
*H04B 17/00* (2006.01)
(Continued)

(52) U.S. Cl.
CPC .............. *H04B 10/548* (2013.01); *H04B 10/07* (2013.01); *G02F 2/002* (2013.01);
(Continued)

(58) Field of Classification Search
CPC . G02F 2/002; G02F 2201/02; G02F 2203/13; G02F 2203/58; G02F 2203/50; H04B 10/548; H04B 10/07; H04B 10/40; G01N 21/3581
See application file for complete search history.

(56) References Cited

U.S. PATENT DOCUMENTS

| 6,348,683 B1 | 2/2002 | Verghese et al. |
| 7,781,736 B2 | 8/2010 | Logan, Jr. et al. |

(Continued)

FOREIGN PATENT DOCUMENTS

| DE | 102006058395 B4 | 9/2008 |
| DE | 102007057850 A1 | 6/2009 |
| WO | WO9320475 A1 | 10/1993 |

OTHER PUBLICATIONS (Direct phase detection in continuous-wave photomixing THz systems, Thorsten Gbobel, IEEE 2008).*

(Continued)

*Primary Examiner* — Shi K Li
*Assistant Examiner* — Mina Shalaby
(74) *Attorney, Agent, or Firm* — Faegre Baker Daniels LLP

(57) ABSTRACT

The invention relates to a system for producing a signal having a variably adjustable time position or phase position, comprising at least one light source for producing a first light component (2) having a first wavelength and a second light component (2') having a second wavelength deviating from the first wavelength and a phase modulator (5) for varying a phase of the first light component (2), wherein the system is designed to produce a beat note signal by superposing the two light components (2, 2') and has a common optical fiber (4) for coupling in both light components (2, 2'), wherein furthermore the phase modulator (5) is arranged at an end or in the course of said optical fiber (4) and is transparent to both light components (2, 2') and is designed to vary the phase of the first light component (2) selectively independently of a phase of the second light component (2') or more intensely than the phase of the second light component (2'). The invention further relates to a use of such a system.

15 Claims, 3 Drawing Sheets

Figure 1:
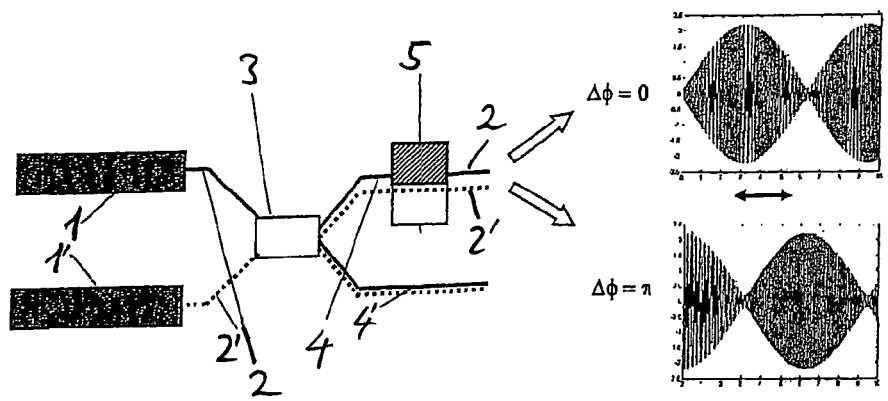

(51) Int. Cl.
 H04B 10/00 (2013.01)
 H04B 10/07 (2013.01)
 G02F 2/00 (2006.01)
 H04B 10/548 (2013.01)
 H04B 10/40 (2013.01)
 G01N 21/3581 (2014.01)

(52) U.S. Cl.
 CPC ....... G02F 2203/58 (2013.01); G01N 21/3581 (2013.01); G02F 2203/50 (2013.01); H04B 10/40 (2013.01); G02F 2203/13 (2013.01); G02F 2201/02 (2013.01)
 USPC .......................................... 398/25; 398/140

(56) References Cited

U.S. PATENT DOCUMENTS

| | | | |
|---|---|---|---|
| 8,064,740 | B2 | 11/2011 | Sartorius et al. |
| 8,494,378 | B2 | 7/2013 | Takasaka et al. |
| 2006/0011840 | A1 | 1/2006 | Bryce et al. |
| 2010/0067918 | A1* | 3/2010 | Federici et al. ............... 398/158 |
| 2010/0072368 | A1 | 3/2010 | Boegli et al. |

OTHER PUBLICATIONS

Al-Mumin, Mohammed et al., "Injection locked multi-section gain-coupled dual mode DFB laser for terahertz generation", Optics Communications, vol. 275, No. 1, May 10, 2007, pp. 186-189.

Brox, Oltaft, "DFB-Laser mit integriert optischer Ruckkopplung fur die optische Signalverarbeitung", Universitatsbibiliothek der TU Berlin: Digitales Respositorium, Apr. 7, 2005 (English title: DFB laser with integrated optical Jerk coupling for the optical signal processing. Document translation downloaded from http://translate.googleusercontent.com/translate_f).

Brox, Olaf, English translation downloaded from http://translate.googleusercontent.com/translate_f.

Gobel, Thorsten et al., "Extern stabilisierte DFB-Laser zur hochauflosenden Dauerstrich-Terahertz-Spektroskopie", Technisches Messen, vol. 75, No. 12, Oct. 1, 2008, pp. 623-630 (English title: Externally stabilized DFB laser for high-resolution continuous-wave terahertz spectroscopy. Document translation downloaded from http://translate.googleusercontent.com/translate_f).

Hong, Cheng et al., "Single-Sideband Modulation Based on an Injection-Locked DFB Laser in Radio-Over-Fiber Systems", IEEE Photonics Technology Letters, vol. 22, No. 7, Apr. 1, 2010, pp. 462-464.

International Search Report and Written Opinion issued in PCT/EP2011/000858, mailed Mar. 16, 2012, 38 pages.

Ogusu, M. et al., "Milimeter-wave WDM sources using two-mode injectin-locked FP lasers", Optics Communications, vol. 251, No. 1-3, Jul. 1, 2005, pp. 75-93.

Sartorius, B. et al., "Continuous wave terahertz systems exploiting 1.5 um telecom technologies", Optics Express, Aug. 17, 2009, vol. 17, No. 17, pp. 15001-15007.

Sinyukov, Alexander M., "Rapid-phase modulation of terahertz radiation for high-speed terahertz imaging and spectroscopy", Optics Letters, Jul. 15, 2008, vol. 33, No. 14, pp. 1593-1595.

Song, Yiqiao et al., "All-optical broadband phase modulation of a subcarrier in a radio over fiber system", Optics Letters, vol. 31, No. 22, Nov. 15, 2006, pp. 3234-3236.

Topcu, S. et al., "A new type of fiber-optic-based interferometric ellipsometer for in situ and real-time measurements", Review of Scientific Instruments, vol. 74, No. 10, Oct. 2003, pp. 4442-4447.

Towers, Catherine E. et al., "Fiber interferometer for simultaneous multiwavelength phase measurement with a broadband femtosecond laser", Optics Letters, vol. 29, No. 23, Dec. 1, 2004, pp. 2722-2724.

Wiberg, Andreas, "Dispersion-Tolerant Millimeter-Wave Photonic Link Using Polarization-Dependent Modulation", Journal of Lightwave Technology, vol. 25, No. 10, Oct. 2007, pp. 2984-2991.

* cited by examiner

ARRANGEMENT FOR GENERATING A SIGNAL HAVING AN ADJUSTABLE TIME POSITION OR PHASE POSITION

The invention relates to an arrangement for generating a signal having a variably adjustable time position or phase position in accordance with the preamble of the main claim. The time-displaceable signal which can thereby be generated is an optical beat note signal or an electrical signal obtained by conversion of such an optical signal or a signal given by electromagnetic radiation of a corresponding frequency.

The setting of the time position and/or phase position of modulated signals is a frequently required functionality in optical and electrical metrology. With interferometric effects, it is a question of the phase position of a light wave, that is of distances in the µm range and times in the fs range. There are already electrically controllable phase shifters on a semiconductor basis for this purpose.

If larger delays in the ns range to ps range, corresponding to migration distances of electromagnetic waves of an order of magnitude from 0.1 mm to 10 cm, are required, the usual solution is to vary the migration distances of electromagnetic waves by mechanical length variations. Movable reflective mirrors, fast switching of distances with graduated lengths, stretching of fibers or utilization of the dispersion of fibers in combination with wavelength coordination are usual possibilities. Such optomechanical delay lines are used e.g. in optical autocorrelation measuring stations, in pump-probe experiments or in optical terahertz systems. Delay lines which require mechanical adjustments are, however, slow, large, heavy, sensitive to blows and expensive. A solution is also desired for delays in the ps range and ns range which is based on compact and robust semiconductor chips with an electrical and fast control.

For this purpose, document DE 10 2006 058 395 A1 proposes an arrangement for generating a signal with a variably adjustable time position or phase position which includes two lasers for generating a first light component having a first wavelength and a second light component having a second wavelength differing from the first wavelength as well as a phase modulator for varying a phase of the first light component, wherein the arrangement is configured to generate a beat note signal by superimposing the two light components. The basis is therefore a superimposition of two laser waves having slightly different wavelengths by which the beat note signal arises whose frequency depends on the wavelength difference. The phase position of the beat note signal can be shifted by selective phase modulation of the one of the laser waves. The phase modulation of laser waves is possible in this respect using semiconductor-based compact electrooptical phase modulators at high frequencies. Depending on the frequency of the beat note signal, the phase modulation can effect a time shift in the ps range or mm range. A phase modulation of one of the laser waves by $\pi$ at a beat frequency of 100 GHz thus likewise shifts the beat note signal by $\pi$, namely by 5 ps or 1.5 mm. At a beat frequency of 10 GHz, a shift of the beat note signal by 50 ps or 15 mm correspondingly results; at 1 THz by 500 fs or 150 µm. The beat note signal thus modulated in time can then be correlated with a signal stable in time or can be converted into an electrical signal by a detection unit and utilized as such. Optical beat note signals can therefore serve as levers to convert fast phase modulations of a laser wave into time modulations or migration distance modulations of signals larger by a multiple.

In the prior art from document DE 10 2006 058 395 A1, the two lasers and the phase modulator are realized on a common chip together with couplers required for the superimposition of the two light components. Such an integrated design of the complete arrangement was necessary in this respect to avoid phase instabilities in individual light paths for the different light portions. Such phase instabilities must be avoided at all costs because they are multiplied to form large time instabilities and path distance instabilities, and indeed to the same degree that the shift of the phase of one of the light components by the desired effect results in a disproportionately larger shift of the beat note signal. This problem is solved in the named prior art by the integrated design on a chip because the individual light paths are thereby very short and very stable in phase. After superimposition of the two light components, phase instabilities are no longer critical since they have an almost identical effect on both light components and practically no longer influence the beat note signal. The beat note signal can therefore also be conducted e.g. in glass fibers without interfering effects occurring. A replacement of the light paths realized in the named prior art on the chip before and between the couplers with optical fibers would, in contrast, not be possible without dramatic effects on the stability of the beat note signal because e.g. the thermal radiation of a hand from a distance of several centimeters heavily influences the light phase in an optical fiber.

It is therefore not possible in the named prior art to use independent components for the lasers, the couplers and the phase modulator which all have to be integrated on the one chip here. This has the consequence of high development costs, on the one hand, because components which are easily available cannot be used and the components integrated on the chip, on the other hand, typically do not have such good properties as corresponding individually optimized components.

It is therefore the underlying object of the invention to propose a corresponding arrangement for generating a signal having a variably adjustable time position or phase position which does not necessarily have to be realized in integrated form on a chip and for whose realization conventional components can be used, in particular already available high-performance lasers or semiconductor lasers tunable in wide wavelength ranges. It is furthermore the object of the invention to propose a method for generating a signal, in which a time position or phase position of this signal can be variably adjusted, which is comparatively simple to realize, which can be carried out with high precision and is less prone to interference.

This object is satisfied in accordance with the invention by an arrangement having the characterizing features of the main claim in conjunction with the features of the preamble of the main claim and by a use of this arrangement in accordance with claim 17. Advantageous embodiments and further developments of the invention result from the features of the dependent claims.

The proposed arrangement also provides at least one light source for generating a first light component having a first wavelength and a second light component having a second wavelength differing from the first wavelength as well as a phase modulator for varying a phase of the first light component and is configured for generating a beat note signal by superimposition of the two light components. This arrangement additionally has a common optical fiber for coupling both light components, with the phase modulator being arranged at an end of this optical fiber remote from the at least one light source or in the course of this optical fiber, and with the phase modulator being transparent for both light components and being configured to vary the phase of the first light component selectively independently of a phase of the second light component or by more than the phase of the second light component. A typically only small wavelength difference between the two wavelengths and a beat frequency of the beat note signal depending thereon can in this respect be selected depending on a desired delay time.

The basic idea thereby realized is to conduct a signal path for both light components largely through a common fiber so that otherwise interfering effects such as changes in refractive indices and polarizations by external influences on fiber optics have almost the same effect on both light components so that the beat note signal remains practically uninfluenced. In this respect, the invention advantageously allows a robust and inexpensive design while using conventional components.

The at least one light source can e.g. be realized by two lasers, preferably single-mode lasers, for producing a respective one of the two light components. Unwanted influences on only one of the light components which could vary the beat note signal in an uncontrolled manner can be particularly easily excluded if instead a dual-mode laser is used for generating both light components. It is particularly advantageous if in this respect at least one of the lasers or if the dual-mode laser can be tuned for varying the wavelength of at least one of the two light components so that a frequency or pulse length of the beat note signal can be adjusted. On the one hand, different frequency ranges can be addressed, e.g. also in the THz range, and, on the other hand, very different time and distance modulations of the beat note signal can then be set with a given control of the phase modulator.

The proposed modulation technique is based on the control of the beat note signal acquired from the two light components. In many cases, however, controllable pulses are required. In an advantageous embodiment of the invention, the arrangement therefore has a pulse compressor connected after the phase modulator which can e.g. be realized by an ultralong optical semiconductor amplifier or, in particular with high performance, by a non-linear glass fiber.

The desired time modulation of the beat note signal, that is a variation of its time position or phase position, is achieved in the proposed arrangement by the selective phase modulator which only or predominantly modulates one of the light components in that the phase of the first light component is varied selectively independently of a phase of the second light component, or more than the phase of the second light component, when the phase modulator is correspondingly controlled. The phase modulator in this respect should preferably be configured to vary the phase of the first light component or a relative phase between the light components by at least $\pi$, preferably by at least $2\pi$. In this respect, the phase modulator should have a speed potential which is as high as possible, preferably up to and into the MHz or GHz range. It is particularly advantageous if the phase of the first light component or the relative phase can also be shifted by a correspondingly configured control unit, also with a period saw-tooth like function, by $2\pi$ respectively or by a multiple thereof. The beat note signal can then be continuously shifted practically as much as desired, and indeed independently of a starting phase which depends on a respective work point of the phase modulator.

With respect to a design which is as simple and as robust as possible, the phase modulator should be controllable purely electrically, that is without any movement of movable parts, for varying the phase of the first light component. For this purpose, different electrooptical phase modulators can be used.

A first possibility is based on the idea of utilizing a very high polarization dependence of many modulators. The (linear) Pockels effect is e.g. generally polarization-dependent. Other effects can also be made polarization-dependent, e.g. if an efficiency of a phase modulator for light of a specific wavelength depends on a distance of this wavelength from a band edge and the band edge for TE-polarized light and TM-polarized light can be designed differently. This is e.g. the case in so-called quantum well structures and strained layer structures. Since waves or wave portions of the same polarization have to be superimposed to generate a beat note, while the light components have to be radiated into the phase modulator at a different and preferably orthogonal polarization for the desired selective phase modulation while utilizing polarization-dependent effects, further measures are necessary for utilizing the polarization dependence of such modulators. A suitable embodiment of the invention provides that the phase modulator is polarization-dependent, with the at least one light source being configured for generating the two light components at different, typically orthogonal polarizations and being connected by the optical fibers to the phase modulator such that the polarizations of the two light components correspond to two main axes of the phase modulator, and with the arrangement having a polarizer arranged after the phase modulator for superimposing transmitted portions of the two light components. The polarizer could under certain circumstances also be replaced with a different arrangement for superimposing light portions of orthogonal polarization, for example by a combination of a mode splitter, of a polarization converter and of a coupler. In this respect, a phase modulator is called polarization-dependent when it has an influence on a phase of a light wave dependent on a polarization of this light wave. In this respect, the directions of the polarization for which the phase modulator respectively effects a defined phase delay or time delay with the given control are called main axes.

The polarizer preferably provided for superimposing the transmitted portions can be realized as a polarization-dependent absorber or as a polarization-dependent amplifier; it is typically a simple polarization filter. A polarization direction of the polarizer for this purpose includes a respective non-vanishing angle with the polarizations of both light components, typical an angle of a respective 45°, but under certain circumstance, also an angle differing from this value or an adjustable angle for compensating intensity differences of the light components. The relative amplitudes of the beat waves can namely be influenced by setting the angle by rotating the polarizer and can in particular be set to the same values, which results in an optimum beat note signal. The polarization filter divides both light components vectorially into a respective portion blocked by the polarizer and into a portion which the polarizer allows to be transmitted so that the transmitted portions of the two light components have the same polarization and can superimpose to form the beat note signal. The phase modulator in this embodiment of the invention can be realized on the basis of a material which has an electrooptical effect more, or preferably only, for light of a polarization or on the basis of a waveguide structure with quantum well semiconductor layers or strained layer semiconductor layers having different band intervals for TE-polarized waves and TM-polarized waves.

Another embodiment of the invention provides that the phase modulator has a wavelength-selective reflector for reflecting the second light component which is transmitting for light of the first wavelength as well as a further reflector for reflecting the first light component, with a phase-modulating region being provided between the two reflectors for varying the phase of the first light component. This phase-modulating region can e.g. be given by a conventional electrooptical phase modulator. The named further reflector can be realized e.g. by a simple mirror coating. This embodiment is in particular to be preferred when it is not possible to generate the two light components with different polarizations, for example on a use of a corresponding dual-mode laser. The second light component whose phase should remain unchanged on a control of the phase modulator is reflected in this embodiment by the wavelength-selective reflector interposed before the phase-modulating region before reaching the phase-modulating region. The first light component, in contrast, is only reflected with the aid of the further reflector after passing through the phase-modulating region and subsequently again passes through the phase-modulating region. By superimposing the two reflected light components at the different reflectors, the beat note signal again results which is composed of a non-phase modulated and a (twice) phase-modulated wave and which can be displaced in a desired manner by controlling the phase-modulating region.

In addition, the phase modulator in this embodiment can have a circulator or a fiber coupler having at least three outputs, with two of these outputs corresponding to an input and an output of the phase modulator, while a third of these outputs is optically coupled to the wavelength-selective reflector. It can thereby be achieved in a simple manner that the light components are supplied to the group of the two reflectors and the phase-modulating region disposed therebetween from the side at which the wavelength-selective reflector is arranged, while the light component reflected there and the light component exiting there again are again superimposed on one another and are conducted to the output of the phase modulator. Input signals and output signals of the phase-modulating region with the two reflectors can thus easily be separated.

The wavelength-selective reflector can e.g. be given by an interference filter or a distributed Bragg reflector (DBR) or a passive feedback laser (PFL) or a DFB (distributed feedback) structure. A different dispersing graded filter can also be used instead. A highly reflective stop band should in this respect in each case be adapted to the second wavelength, while a non-reflective region should naturally include the first wavelength.

Phase instabilities must again be avoided as much as possible at the point where the two light components each have an individual beam path. For this purpose, the wavelength selective reflector and/or the further reflector can, for example, be applied directly to modulator facets, that is surfaces of the phase-modulating region, for example vapor deposited or adhesively bonded. This applies in particular when a simple interference graded filter is used as the wavelength-selective reflector. A monolithic integration having DBR structures or DFB structures is also advantageous as a wavelength-selective reflector in an III-V material system or a hybrid integration having dispersing structures on the basis of inexpensive polymers or of a silicon material. With respect to a phase stability which is as good as possible, it is at least advantageous if the wavelength-selective reflector or the further reflector or preferably both reflectors form(s) a monolithic structure with the phase-modulating region. The further reflector can in the simplest case be realized by a simple mirror coating of the corresponding modulator facet.

Irrespective of how the selective phase modulator is exactly realized, an advantageously low proneness of the set time position or phase position of the generated signal to interference in optical paths of the arrangement which might result e.g. due to temperature differences or mechanical strains, results due to the common optical fiber for both components in the proposed arrangement because separate paths for the two light components are very largely avoided.

Typically, the proposed arrangement will have a detection unit downstream of the phase modulator for converting the beat note signal into an electrical signal or a signal given by an electromagnetic wave. This signal then has a time position or phase position adjustable in accordance with the beat note signal and can e.g. be used for the time control of an electrical measurement system, for example in relative time correlation to a signal controlling the phase modulator. In this respect, the detection unit can be given be a detector or can include a plurality of detectors.

A particularly advantageous arrangement results when a coupler connected before the phase modulator is additionally provided for decoupling a portion of a beat note from both light components not yet modulated by the phase modulator, with the detection unit preferably being configured to detect both this portion and the beat note signal exiting the phase modulator. Expediently, the detection unit should then be suitable for determining a correlation of the named decoupled portion and of the beat note signal at a modulation of the phase of the first light component and thus of the time position or phase position of the beat note signal. A further coupler can be provided for this purpose for the superposition of the named portions and of the modulated beat note signal.

An expedient sensor arrangement results when in this case a specimen is brought into a beam path of the named decoupled portion or into a beam path of the beat note signal shifted by the phase modulator. A change in a correlation signal caused by the specimen and determined by the detection unit can then be determined and thus a conclusion can be drawn on properties of the specimen.

In a particularly advantageous application of the invention, the arrangement has a non-linear component, e.g. a photomixer, for generating an electromagnetic radiation at a frequency which corresponds to a beat note frequency of the beat note signal. This frequency is preferably in the THz range. The non-linear component can therefore in particular form a THz transmitter. The arrangement can then be used e.g. for spectrometers, reflectometers or other sensor arrangements, in particular for THz radiation. In this respect, a radiation portion decoupled before the phase modulator can preferably be utilized for an activation of a corresponding receiver to allow a coherent detection of the radiation. The arrangement can therefore in particular form a coherent THz measurement system. The general design of such a THz measurement system is described, with the exception of the generation of the time-shiftable activation signal described here, for example in the document U.S. Pat. No. 6,348,683 B1. Transmitters and receivers can naturally also be swapped over so that the radiation portion decoupled before the phase modulator is used for activating the transmitter, while the portion shifted in its time position and phase position is used for activating the receiver. The non-linear component for generating the electromagnetic radiation does not necessarily have to be acted on by the original beat note signal, but can rather instead also be exposed to a compressed pulsed signal acquired therefrom. The electromagnetic radiation thus produced can naturally also have or include different frequencies than the beat note frequency.

In view of all this, advantageous processes result by a use of an arrangement of a described kind for generating a signal corresponding to the beat note signal or acquired by conversion of the beat note signal, with the time position or phase position of this signal being changed by controlling the phase modulator, which can also be called a phase shifter. This process can in particular be a measurement process for examining specimens, in particular a process in which the specimen is exposed to THz radiation which can be acquired by activating a THz transmitter by the beat note signal or by a decoupled portion of the beat note signal. With such measurement processes, a respective dependence of a detector signal on the time position or phase position of the signal can be evaluated.

Figure 2:
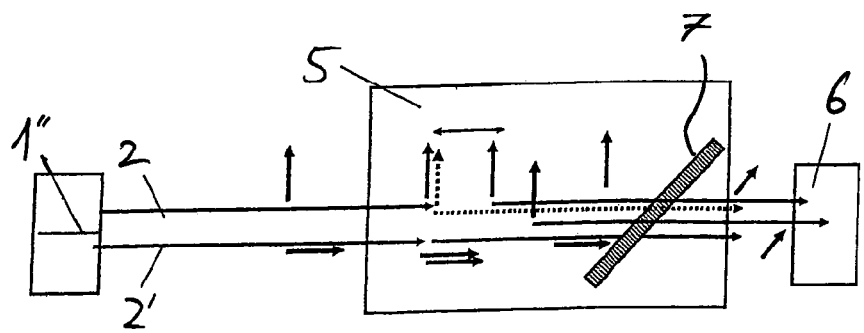
Figure 3:
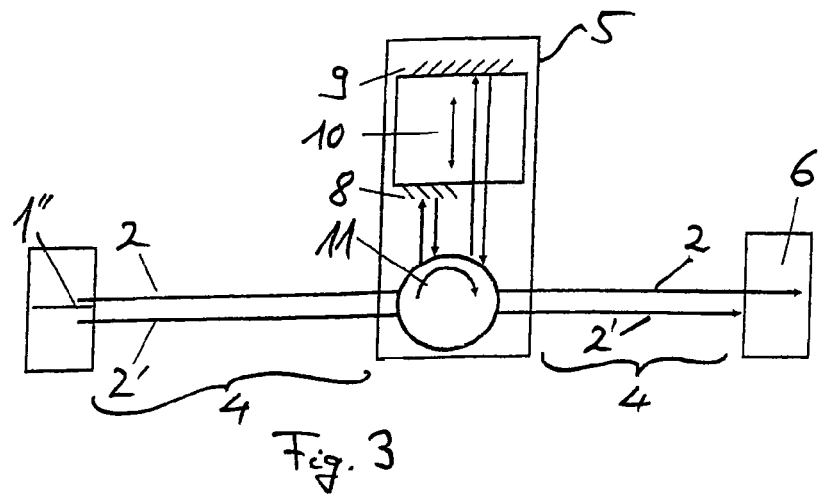
Figure 4:
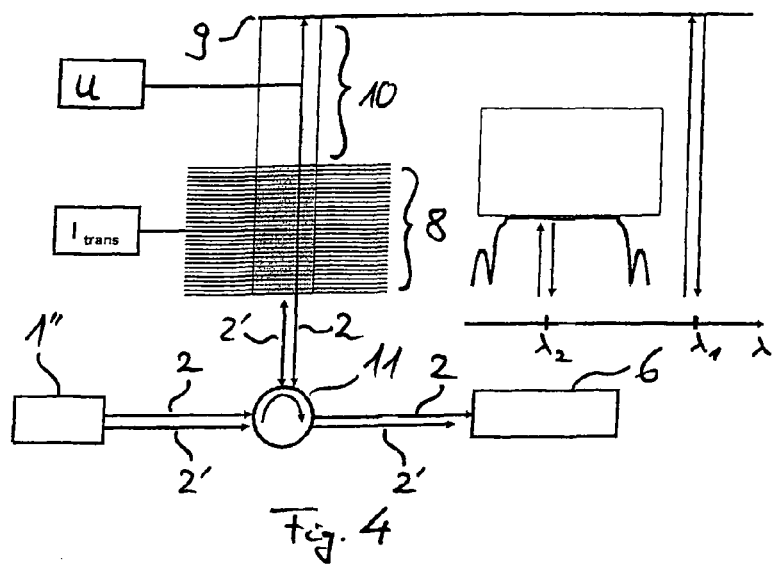
Figure 5:
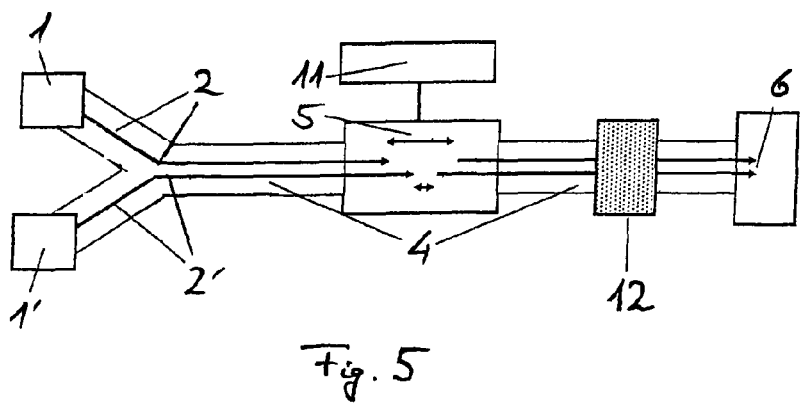
Figure 6:
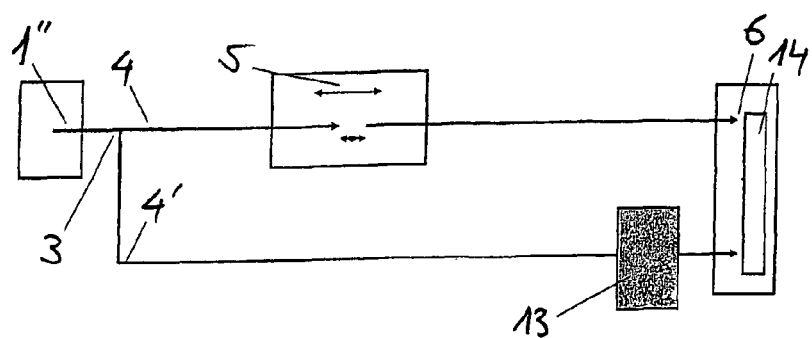
Figure 7:
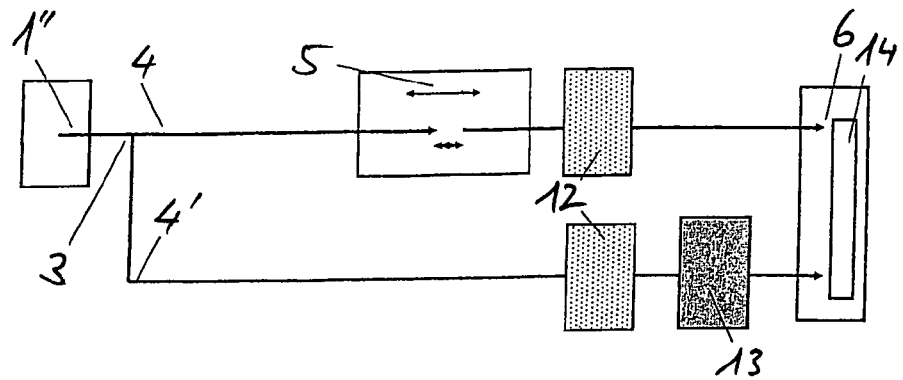
Figure 8:
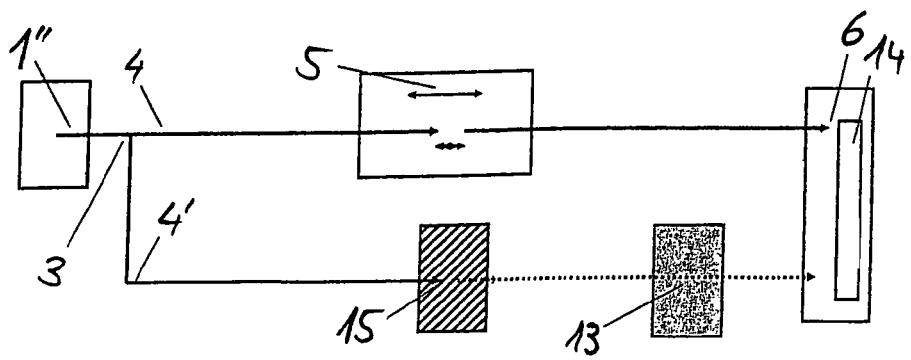

Embodiments of the invention will be explained in the following with reference to FIGS. 1 to 8. There is shown FIG. 1 a schematic representation of the operation of an arrangement in accordance with the invention;

FIG. 2 an embodiment of such an arrangement likewise in a schematic representation;

FIG. 3 a comparable arrangement in another embodiment in a corresponding representation;

FIG. 4 a modification of the embodiment of FIG. 3 likewise in a schematic representation;

FIG. 5 a likewise schematically shown comparable arrangement which additionally includes a pulse compressor;

FIG. 6 a schematically shown sensor arrangement;

FIG. 7 a correspondingly shown similar sensor arrangement which additionally has two pulse compressors; and FIG. 8 a sensor arrangement which is a measurement structure for a coherent THz detection in a schematic representation corresponding to FIGS. 6 and 7.

An arrangement for generating a beat note signal is shown in a schematic manner in FIG. 1, with a time position or phase position of this beat note signal being modulable, that is variably adjustable. This arrangement has two single-mode lasers 1 and 1' of which at least one is tunable. A first light component 2 which exits the laser 1 and a second light component 2' generated by the laser 1' are superimposed in an optical coupler 3. In this respect, the first light component 2 has a first wavelength, while the second light component 2' has a second wavelength slightly different form the first wavelength so that a beat note signal is generated by the coupler 3. This beat note signal, which contains both light components 2 and 2' is coupled into a respective common optical fiber 4 and 4' at two outputs of the coupler 3. A selective phase modulator 5 is arranged at an end or in the extent of the optical fiber 4. This phase modulator 5 is transparent for both light components 2 and 2' and has the property of selectively varying a phase of the first light component 2 independently of a phase of the second light component 2' or of at least varying it much more than the phase of the second light component 2', and indeed in dependence on a control signal with which the phase modulator 5 can be controlled. The time position or phase position of the beat note signal exiting the optical fiber 4 or the phase modulator 5 can thereby be varied in dependence on the control of the phase modulator 5, which is shown in two diagrams at the right in FIG. 1 where the beat note signal is shown once for a vanishing phase shift (top) and once for a phase shift of the first light component 2 by π (bottom).

The phase modulator 5 is an electrooptical phase shifter which is controllable purely electrically, that is without the movement of moving parts, and with which the phase of the first light component 2 can be shifted by at least 2π. In this respect, the phase modulator 5 can also be controlled at very high frequencies in the MHz range or GHz range, with the change in the relative phases between the two light components 2 and 2' (designated as ΔΦ at the right in FIG. 1) also being able to be adjustable by means of a correspondingly programmed control unit in saw tooth form by a respective 2π. The coupler 3 in the arrangement shown in FIG. 1 also serves the decoupling of a portion of a beat note from both light components 2 and 2' not yet modulated by the phase modulator 5, with this portion being conducted through the optical fiber 4' and being able to serve e.g. as a reference signal.

Instead of the two lasers 1 and 1', in other embodiments, a dual-mode laser can also be used for generating the two light components 2 and 2' and thus for generating the beat note signal, with the coupler 3 then being able to be dispensed with provided that no phase-shifted reference signal is required.

An embodiment for such an arrangement is shown in FIG. 2. Recurring features are again marked here and in the further Figures with the same reference numerals. A dual-mode laser 1" which is connected to the phase modulator 5 by the common optical fiber 4 for both light components 2 and 2' here serves as the light source for the two light components 2 and 2'. The dual-mode laser 1", instead of which through another light source can also be used for generating two light waves of different wavelengths, is designed such that at least the wavelength of one of the two light components 2 and 2' can be adjusted. The arrangement of FIG. 2 furthermore has a detection unit 6 disposed after the phase modulator 5 for converting the beat note signal exiting the phase modulator into an electrical signal. The detection unit 6 can again be optically coupled to an output of the phase modulator 5 by a common optical fiber for both light components 2 and 2' or in another manner. An electrical signal is thus generated whose time position or phase position can be adjusted in accordance with the time position or phase position of the optical beat note signal by means of the phase modulator 5. The electrical signal thus generated can be used e.g. for the time control of an electrical measured signal.

The phase modulator 5 in the embodiment shown in FIG. 2 is polarization-dependent, with the dual-mode laser 1" generating the two respective monochromatic light components 2 and 2' having slightly different wavelengths and having orthogonal polarizations being coupled to the phase modulator 5 by the optical fiber 4 so that the polarizations of the two light components 2 and 2' correspond to two main axes of the polarization-dependent phase modulator 5' A polarizer 7 for superimposing portions of the two light components 2 and 2' transmitted through the polarizer 7 is provided at an output of the phase modulator 5 which only shifts a phase of the first light component 2 due to its polarization dependence. The polarizer 7, which can be realized by a simple polarization filter in the simplest case, is arranged in this respect such that a polarization direction of the polarizer 7 respectively includes a non-vanishing angle of typically 45° with the polarizations of both light components 2 and 2' so that a beat note signal from the transmitted portions of the two light components 2 and 2' exits the polarizer 7 whose time position and phase position can be adjusted by controlling the phase modulator 5. The polarizer 7 can also be designed as rotatable so that the named angles can be adjusted to compensate intensity differences between the light components 2 and 2'. Instead of a polarization-dependent absorber, a polarization dependent amplifier can also be used as the polarizer 7. The phase modulator 5 is only realized for light of one polarization on the basis of a material with an electrooptical effect or by a waveguide structure with quantum well semiconductor layers or strained-layer semiconductor layers having different band intervals for TE-polarized and TM-polarized waves.

Another embodiment of a corresponding arrangement for generating a signal shiftable in time or with respect to its phase position is shown in FIG. 3. The dual-mode laser 1" generates the two light components 2 and 2' in this case with the same polarization so that the phase modulator 5 has to be designed differently to be able selectively to modulate the phase of the first light component 2. In this case it has a wavelength-selective reflector 8 for reflecting only the second light component 2' which is transmitting for light of the first wavelength as well as a further reflector 9 for reflecting the first light component 2. A phase-modulating region 10 for varying the phase of the first light component 2 is provided between the two reflectors 8 and 9, is realized by a conventional phase shifter and is controllable by application of electrical voltage such that it delays the phase of the first light component 2 to the desired degree.

The wavelength-selective reflector 8 and the further reflector 9 form a monolithic structure with the phase-modulating region 10, with the further reflector 9 being realized by a simple mirror coating of an upper facet of the phase shifter. The wavelength-selective reflector 8 is here given by a simple interference filter, with a highly reflective stop band being adapted to the second wavelength, whereas a non-reflective region of this reflector 8 includes the first wavelength. Another dispersing graded filter can naturally also be used instead of the interference filter. The phase modulator 5 has a circulator 11 having three outputs to direct the light coming from the dual-mode laser 1" to the phase-modulating region 10 having the two reflectors 8 and 9 and in turn to conduct the light reflected back from there to an output of the phase modulator 5 from which it is guided to the detection unit 6. Two of these outputs correspond to an input and to the output of the phase modulator 5, whereas a third output is optically coupled to the wavelength-selective reflector 8. In modifications of the arrangement shown here, a fiber optic coupler having at least three outputs could also be used instead of the circulator 11.

In FIG. 4, a modification of the arrangement of FIG. 3 is shown in which the wavelength-selective reflector 8 is given by a PFL to which a control current $I_{trans}$ is applied which is selected so that the PFL has the desired transmission and reflection properties. The stop band of the PFL within which the wavelength $\lambda_2$ of the second light component 2' lies is illustrated to the right next to the reflector 8. The phase shifter which forms the phase-modulating region 10 is controlled in a usual manner by a control voltage U to delay the phase of the first light component 2 to the desired degree. The wavelength $\lambda_1$ of the first light component is outside the stop band of the PFL so that the first light component 2 is reflected at the further reflector 9 also realized again here by a simple mirror-coating. The wavelength-selective reflector 8 can finally also be realized by a DFB structure or by a DBR instead of by a PFL. The wavelength-selective reflector 8 and the further reflector 9 also form a monolithic structure with the phase-modulating region 10 here, with a hybrid structure also being conceivable in which the wavelength-selective reflector 8 having III-V semiconductor material, in polymers or based on silicon, is integrated with the phase-modulating region 10.

In FIG. 5, an arrangement comparable with the already described arrangements is shown in which recurring features are again characterized by the same reference numerals. In addition, an electrical control 11 for controlling the selective phase modulator 5 is shown here. In this embodiment, a pulse compressor 12 which reshapes the beat note signal to pulses is connected between the phase modulator 5 and the detection unit 6. A signal can therefore be generated from sequential pulses using this arrangement whose time position can be varied by the phase modulator 5 by a corresponding control by means of the electrical control 11. The pulse compressor 12 is an ultralong optical semiconductor amplifier or a nonlinear glass fiber.

It is shown in FIG. 6 how an arrangement of the described kind can be expanded to a sensor arrangement for examining a specimen 13. Recurring features are here again also provided with the same reference numerals and no longer have to be described separately. Instead of the dual-mode laser 1", another light source can naturally also be used for generating the two light components 2 and 2' of slightly different wavelength, for example the single-mode lasers 1 and 1' shown in FIGS. 1 and 5. The coupler 3 here serves the decoupling of a portion of the beat note signal which is obtained by superposition of the two light components 2 and 2'. The detection unit 6 is configured in this case to detect both this decoupled portion and the beat note signal exiting the phase modulator 5 and includes a correlator 14 for determining a correlation of both on a modulation of the phase of the beat note signal in the optical fiber 4 by modulating the phase of the first light component in the phase modulator 5. The specimen 13 is here arranged in a beam path of the portion decoupled by the coupler 3 so that the beat note signal exiting the phase modulator 5 serves as a reference signal. The specimen could equally well be arranged in the beam path of the beat note signal exiting the phase modulator 5 and the decoupled portion guided through the optical fiber 4' could serve as the reference signal. In both cases, a change of a correlation signal caused by the specimen 13 and determined by the detection unit 6 can be determined by means of the detection unit 6 with the correlator 14.

A sensor arrangement is shown in FIG. 7 which only differs from the sensor arrangement of FIG. 6 in that a respective pulse compressor 12 is connected both in an extent of the optical fiber 4' in front of the specimen 13 and behind an output of the phase modulator 5 so that here both the signal passing through the specimen 13 and the reference signal, whose time position can be varied by the phase modulator 5, is respectively reshaped to a sequence of pulses.

Another sensor arrangement is shown in FIG. 8 which uses largely the same components as the two sensor arrangements previously described. This sensor arrangement additionally has a photomixer 15 which is realized by a non-linear component which is activated by the portion of the beat note signal decoupled by the coupler 3 and which forms a THz transmitter. Electromagnetic radiation is generated by the photomixer 15 which has a frequency which corresponds to the beat note frequency of the beat note signal and which should be in the THz range here, which in particular designates the frequency range from 0.1 THz to 10 THz. The detection unit 6 is in this case given by a THz receiver which is activated by the optical beat note signal which is conducted through the optical fiber 4 and whose phase position is set by the phase modulator 5. The phase modulator 5 could naturally also be connected before the photomixer 15, that is in an extent of the optical fiber 4'. The photomixer 15 is then activated by the phase-shifted beat note signal which exits the phase modulator 5, while a corresponding beat note whose phase is not manipulated serves the activation of the THz receiver.

The invention claimed is:

1. A THz measurement system comprising:
a THz transmitter having a light-sensitive element;
a THz receiver having a light-sensitive element; and
an arrangement for generating a signal having a variably adjustable time position or phase position, the arrangement including:
at least one light source for generating a first light component having a first wavelength and a second light component having a second wavelength differing from the first wavelength; and
a phase modulator for varying a phase of the first light component, the phase modulator arranged between the at least one light source and the light-sensitive element of the THz receiver or between the at least one light source and the light-sensitive element of the THz transmitter, a common optical fiber for coupling in the first and second light components, the phase modulator being arranged at an end of the optical fiber remote from the at least one light source or being arranged in the extent of the optical fiber, the phase modulator being transparent for both light components and being configured to vary the phase of the first light component selectively independently of a phase of the second light component or more than the phase of the second light component, wherein the arrangement is configured for generating a beat note signal by superimposing the two light components, wherein the THz transmitter and THz receiver are configured to be activated by the beat note signal or by a decoupled portion of the beat note signal or by an optical signal which results by reshaping of the beat note signal or of a decoupled portion of the beat note signal, the arrangement further including a coupler connected before the phase modulator for decoupling a portion of a beat note from the first and second light components not yet modulated by the phase modulator, with either the THz receiver being activated by the portion decoupled before the phase modulator and the THz transmitter being activated by the beat note signal exiting the phase modulator or the THz transmitter being activated by the portion decoupled before the phase modulator and the THz receiver being activated by the beat note signal exiting the phase modulator.

2. The THz measurement system of claim 1, wherein the at least one light source comprises two lasers or a dual-mode laser.

3. The THz measurement system of claim 2, wherein at least one of the lasers or the dual-mode laser is tunable for varying the wavelength of at least one of the light components.

4. The THz measurement system of claim 1, wherein the phase modulator is electrically controllable without mechanical movement of movable parts for varying the phase of the first light component and is configured to vary the phase of the first light component by at least $\pi$.

5. The THz measurement system of claim 1, wherein the phase modulator is polarization dependent, with the at least one light source being configured for generating the two light components with different polarizations and being connected by the optical fiber to the phase modulator such that the polarizations of the two light components correspond to two main axes of the phase modulator, and with the arrangement having a polarizer arranged after the phase modulator for superimposing transmitted portions of the two light components.

6. The THz measurement system of claim 1, wherein the phase modulator further comprises a wavelength-selective reflector for reflecting the second light component which is transmitting for light of the first wavelength, and a further reflector for reflecting the first light component, with a phase-modulating region for varying the phase of the first light component being provided between the two reflectors.

7. The THz measurement system of claim 6, wherein the phase modulator furthermore has a circulator or a fiber optic coupler having at least three outputs, with two of the outputs corresponding to an input and to an output of the phase modulator, and a third one of the outputs is optically coupled to the wavelength-selective reflector.

8. The THz measurement system of claim 6, wherein the wavelength-selective reflector comprises an interference filter or a DBR.

9. The THz measurement system of claim 6, wherein at least one of the wavelength-selective reflector and the further reflector form a monolithic structure with the phase-modulating region.

10. The THz measurement system of claim 1, wherein the arrangement further comprises a pulse compressor connected after the phase modulator.

11. The THz measurement system of claim 1, wherein the THz receiver forms a detection unit connected after the phase modulator for converting the optical beat note signal into an electrical signal.

12. The THz measurement system of claim 11, wherein the detection unit is configured to detect both the portion decoupled by the coupler and the beat note signal exiting the phase modulator.

13. The THz measurement system of claim 1, wherein the THz measurement system forms a non-linear component for generating electromagnetic radiation at a frequency corresponding to the beat note frequency of the beat note signal which forms the THz transmitter.

14. The THz measurement system of claim 1, further comprising a specimen arranged such that the specimen influences a signal that results by reshaping the beat note signal or a decoupled portion of the beat note signal.

15. A method of using the THz measurement system of claim 1, the method comprising:
generating a signal corresponding to the beat note signal or acquired by converting the beat note signal; and
controlling the phase modulator to vary a time position or phase position of the generated signal.

* * * * *